Figure 1:
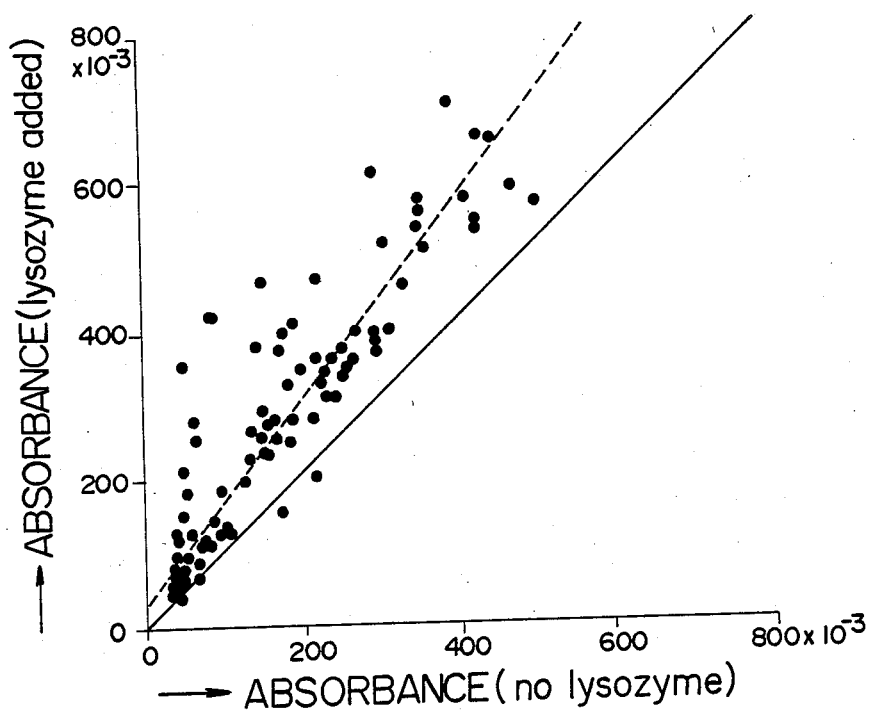

United States Patent [19]
Okuda et al.

[11] Patent Number: 4,920,045
[45] Date of Patent: Apr. 24, 1990

[54] DETECTION OF OCCULT BLOOD IN FECES

[75] Inventors: Shoji Okuda, Nagaokakyo; Kazuo Uchida, Kobe, both of Japan

[73] Assignee: Kyoto Medical Science Laboratory, Kyoto, Japan

[21] Appl. No.: 247,616

[22] Filed: Sep. 22, 1988

[51] Int. Cl.$^5$ .................... G07N 53/00; C07G 15/00; C07K 3/00; G01N 33/72
[52] U.S. Cl. ........................................ 435/7; 435/268; 435/269; 436/66; 436/175; 436/177; 436/825; 436/815
[58] Field of Search .................... 435/7, 268, 269, 272; 436/66, 175, 177, 825, 815

[56] References Cited

U.S. PATENT DOCUMENTS

| 4,277,250 | 7/1981 | Melnick et al. | 435/28 |
| 4,582,811 | 4/1986 | Pucci et al. | 436/548 |
| 4,683,197 | 7/1987 | Gallati | 435/7 |

OTHER PUBLICATIONS

Ueda et al, Preparation of High-Purity Human Transferrin, Dec. 20, 1984, Patent Abstracts of Japan, vol. 8, No. 279 (C-257) (1716).

Primary Examiner—Esther M. Kepplinger
Assistant Examiner—Laurie A. Scheiner

[57] ABSTRACT

A method for detection of occult blood in a fecal sample which comprises acting a glycosidase type bacteriolytic enzyme on the fecal sample and subjecting the resulting fecal sample to simultaneous detection of hemoglobin, preferably in combination with transferrin, by an immunological measurement procedure.

4 Claims, 4 Drawing Sheets

DETECTION OF OCCULT BLOOD IN FECES

The present invention relates to detection of occult blood in feces. More particularly, it relates to an immunological method for detection of blood components in human or animal digestion organs for the diagnostic purpose such as screening of cancer or ulcer, and a detection instrument usable in such method.

For the diagnostic purpose such as finding of abnormalities (e.g. cancer, ulcer) in digestion organs at an early stage, detection of hemoglobin as a representative blood protein from samples of human or animal feces is effected chemically or immunologically. In general, chemical detection is inferior to immunological detection, since the former is quite sensitive and tends to produce too many false positive results. Further, chemical detection comprises detection of a peroxidase activity of hemoglobin in the blood, while a peroxidase activity is also found in meats and vegetables; strict restriction of a diet is thus required prior to its application for assurance of an exact analysis.

For immunological detection, there has recently been developed a method for detection of occult blood in a human fecal sample by the utilization of an antigen-antibody reaction between human hemoglobin and anti-human hemoglobin antibody [Adams: Ann.Clin.Lab.Sci., 4, 343 (1974)]. For instance, a fecal sample is applied onto a filter paper and mixed with carrier particles sensitized with anti-human hemoglobin antibody, followed by observation of the agglutination state of the carrier particles in the mixture [Japanese Patent Publication (unexamined) No. 137064/86]. Further, for instance, a sample of feces is contacted with a hydrophobic resin, and hemoglobin adsorbed onto the resin is subjected to antigen-antibody reaction with an enzymelabeled antibody reagent, followed by coloring [Japanese Patent Application No. 69598/85].

Generally, hemoglobin is apt to accept the action of digestive enzymes or proteases produced by intestinal bacteria so that its detection by an immunological method becomes difficult. Particularly, immunological detection of hemoglobin in feces comprises the following basic problems: (a) the immunological reactivity of hemoglobin is lowered due to conjunction of hemoglobin with viscous components (i.e. muco substances) secreted from digestion organs and cell wall components of intestinal bacteria and (b) hemoglobin is apt to be decomposed by the action of intestinal bacteria so that its amount is decreased with lapse of time.

In addition, anti-hemoglobin antibody has usually so low titer and affinity that a considerable time is needed until the reaction between hemoglobin and anti-hemoblogin antibody proceeds to an extent sufficient for detection or measurement.

In order to overcome the above drawbacks, there is now provided a method for detection of occult blood in human or animal feces comprising applying a glycosidase type cell wall lytic enzyme (hereinafter referred to as "bacteriolytic enzyme") to a fecal sample to detect immunologically hemoglobin, preferably in combination with transferrin.

That is, the method according to the invention comprises applying a glycosidase type bacteriolytic enzyme to a sample of feces to release hemoglobin from its conjuction with viscous components secreted from digestion organs as well as cell wall components of intestinal bacteria and prevent the decomposition of hemoglobin by intestinal bacteria, thus leading to solve the above problems (a) and (b), and immunologically detecting hemoglobin, preferably in combination with transferrin.

When a glycosidase type bacteriolytic enzyme is mixed with a fecal sample, the enzyme prevents the decomposition of hemoglobin with intestinal bacteria for a long period of time. In addition, said enzyme can detach hemoglobin from its conjunction with viscous components as well as cell wall components within a short time and contributes in recovery of the immunological reactivity of hemoglobin.

As the bacteriolytic enzyme, there may be used any one of glycosidase type including enzyme F1 and enzyme 32 produced by Streptomyces albus G, enzyme $E_1$, enzyme $E_2$ and enzyme F2 produced by Streptomyces griseus and enzyme Mu I and enzyme Mu II produced by Streptomyces globisporus 1829, lysozyme Ch produced by Chalaropsis sp., bacterial lysozyme produced by Bacillus subtilis K-77, enzyme B produced by Bacillus subtilis YT-25, FBa-lysin produced by Myxococcus xanthus, etc. These enzymes are commonly known, for instance, as described on Hunazu et al: "Youkinkouso" (Bacteriolytic enzyme), page 93 (1983) and also readily available on the market. For instance, lysozyme obtained from the white of egg (manufactured by Sigma) can be favorably employed for the purpose of this invention.

Application of the bacteriolytic enzyme to a fecal sample may be effected by various ways. For instance, the fecal sample is impregnated or dissolved in a solution of said enzyme, the fecal sample is inserted into an agar gel vessel containing said enzyme for absorption, or the fecal sample is spread onto a filter paper containing said enzyme. The above application is usually effected at a temperature of room temperature (about 15° C) to 37° C. In the application, the enzyme is normally used in the form of an aqueous solution (e.g. 0.1 M Tris buffer containing sodium chloride and having a pH of 7.2), for instance, in a concentration of about 0.2 to 0.4 %.

Detection from a fecal sample may be carried out only on hemoglobin. As stated above, however, its detection may take sometimes a considerable time for obtaining a sufficient sensitivity. From this viewpoint, it is advantageous to effect detection of hemoglobin in combination with any other proper blood protein, i.e. to detect occult blood as the total amount of hemoglobin and any other blood protein as seen in hemorrhage of digestion organs. For this purpose, study was made on various blood proteins in hemorrhage, and as the result, it was ascertained that among various blood proteins including albumin, immunoglobulin, fibrinogen, alphal-antitrypsin, alpha2-macroglobulin, haptoglobulin, transferrin, etc., transferrin is the most suitable, because it is leaked out on hemorrhage of digestion organs with high selectivity and highly resistant to intestinal bacteria. Transferrin is usually contained in an amount of about 250 mg/dl in blood, this amount being nearly 1/60 of the amount of hemoglobin but still possible to detect by an immunological method, and gives absorbance proportional to concentration over a broad range.

The detection in the invention may be effected by a per se conventional immunological procedure, of which some typical examples are shown below.

Method I (Stick EIA (Enzyme Immunoassay) method):

As a collector for feces, there is used a collecting spoon or spatula made of a hydrophobic plastic material (e.g. polyethylene, nylon, polyvinyl chloride) and having a groove(s) at the inner surface of the reservoir or collecting portion. Commercially available anti-human hemoglobin antibody (Dako K.K.) (50 μg/ml) and anti-human transferrin antibody (Dako K.K.) (12.5 μg/ml) are respectively added to a tris buffer solution (pH, 8.4; 0.05 M) to make respectively 200 and 800 fold dilutions. The reservoir or collecting portion of the collector is dipped in the solution, allowed to stand at 4 to 8° C. overnight and dried at room temperature to make it coated with said antibodies.

Different loci of feces are thrusted with the collector. After removal of excess feces by the use of a toilet papers, the feces (about 10 mg) remained in the groove are used as the sample.

Separately, commercially available agarose is added to a NaCl-phosphate buffer solution (pH, 7.2; 0.1 M) while heating to make its 2 % solution. After cooling to 60° C., lysozyme as the bacteriolytic enzyme and $NaN_3$ as the stabilizer and the preservative for proteins are added thereto to make respective concentrations of 3 mg per ml and 0.1 % by weight. The resultant mixture (1 ml) is poured into an agar gel vessel and cooled for gelation.

The collector is inserted into the agar gel vessel, made fixed and allowed to stand for a certain period of time, i.e. not less than 2 hours (usually from 2 hours to one week), during which the fecal sample is diffused into the agar gel, and the hemoglobin conjugated with viscous components and cell wall components are released by the action of lysozyme to be ready to exert its immunological reactivity. In this way, hemoglobin and transferrin in the fecal sample are respectively caught by the anti-hemoblogin antibody and the anti-transferrin antibody at the inner surface of the reservoir or collecting portion. Since lysozyme and $NaN_3$ can act also as the preservatives, it is possible to keep the fecal sample in a preserved condition. In addition, the fecal sample in the above preserved condition is substantially free from any bad smell and retained in a good sanitary state. Thus, it is suitable for sampling at a large scale.

Separately, an enzyme-labeled antibody reagent (i.e. a solution comprising alkali phosphatase-labeled anti-human hemoglobin antibody and alkali phosphatase-labeled anti-human transferrin antibody) is prepared according to a per se conventional method [Yoshitake et al: "Meneki Jikken Ho XI" (Immunological Experimental Methods XI), pp. 3497-3519 (1982)]. The solution comprising alkali phosphatase-labeled anti-human hemoglobin antibody (1500 μg/ml) and alkali phosphatase-labeled anti-human transferrin antibody (1500 μg/ml) are added to a NaCl-phosphate buffer solution containing 5 % bovine albumin and 0.5 mM magnesium chloride to take an enzyme-labeled antibody solution of 500 fold dilutions.

The collector carrying the fecal sample thereon is taken out from the agar gel vessel, washed with deionized water to remove the feces attached thereto and subjected to antigen-antibody reaction at 37° C for 60 minutes in a test tube containing 0.25 ml of the enzyme labeled antibody solution. Then, the collector is washed well with deionized water and submitted to measurement of alkali phosphatase by the Kind-King method [Kind et al: J. Clin. Pathol., 7, 322 (1954)]. The collector is incubated at 37° C. for 30 minutes in a test tube containing a phenylphosphoric acid substrate liquid (0.3 ml), combined with a coloring agent (0.3 ml) and subjected to visual measurement of color phase (e.g. red color).

Method II (ELISA (Enzyme-Linked Immunosorbent Assay) method):

A thick filter paper is impregnated with a NaCl-phosphate buffer solution (pH, 7.2; 0.1 M) containing lysozyme as the bacteriolytic enzyme and $NaN_3$ respectively in concentrations of 4 mg/ml and 1 mg/ml, followed by drying. Onto this filter paper, a small amount of feces is lightly coated by a spatula to make a filter paper sample. Alternatively, the above prepared solution (each 1 ml) is charged in a small bottle to which a small amount of feces is charged to make a solution sample. On each sampling, the amount of feces are desirous to be constant (about 10 mg).

One hundred ul of a tris buffer solution (pH, 8.4; 0.05 M) containing anti-human hemoglobin antibody (Dako K.K.) (50 μg/ml×200 fold dilution) and anti-human transferrin antibody (Dako K.K.) (12.5 μg/ml×800 fold dilution) are admitted into each well on a ELISA microplate, and the microplate is allowed to stand at 4 to 8° C. overnight for coating with the antibodies. The microplate is washed with deionized water, and 100 ul of a NaCl-phosphate buffer solution (pH, 7.2; 0.1 M) containing 1 % bovine albumin are admitted into each well. The punched pieces (each 5 mm in diameter) of the filter paper sample as above prepared are put in each well one by one, or the solution sample as above prepared is charged in each well by 50 μl. Then, antigen-antibody reaction is carried out at 37° C. fot 60 minutes.

The microplate is well washed with deionized water, and 100 ul of an alkali phosphatase labeled antibody solution containing anti-human hemoglobin antibody (1500 μg/ml×500 fold dilution) and anti-human transferrin antibody (1500 μg/ml×500 fold dilution) is admitted into each well, followed by incubation at 37° C for 60 minutes to effect antigen-antibody reaction. The microplate is again washed well with deionized water, and an alkali phosphatase substrate liquid (each 100 μl) for the Kind-King method is admitted into each well, followed by reaction at 37° C. fot 30 minutes. The reaction is interrupted with the addition of a coloring agent (each 100 μl), and measurement of color phase is made by macroscopic observation or by the use of a photometer.

In both methods as above mentioned, it is recommended to use reference for judgement. Namely, a mixture of the heparinized whole bloods taken from a plural number of healthy persons is diluted with deionized water to make a 300,000 fold dilution, and each 50 μl of the dilution is subjected to judgement of the color phase for reference.

In the immunological method of the invention, detection of about 2.5 to 5 p82 g/g feces in terms of hemoblogin is usually judged as positive.

EXPERIMENT 1

Detection of hemoglobin in the samples of plural feces (129 persons) with or without addition of lysozyme was conducted according to the ELISA method. The absorbance as determined by the use of a spectrophotometer is plotted in FIG. 1 of the accompanying drawings wherein the abscissa indicates the absorbance of the samples in case of using lysozyme and the ordinate indicates that of the samples in case of not using lysozyme.

It is clear from the results that the absorbance of the samples in case of using lysozyme are larger (above the 45° line) than that of the samples in case of not using lysozyme. Thus, hemoglobin is more completely detected in the former. An absorbance of about 100 to 200 ($\times 10^{-3}$) is usually taken as the lower limit of "positive" in a conventional standard method. A considerable number of samples judged as "negative" in case of not using lysozyme are judged as "positive" in case of using lysozyme, thus indicating the enhancement of precision in the latter.

EXPERIMENT 2

A whole blood was added to a 25 % aqueous fecal sample obtained by mixing the feces provided by 30 healthy persons to make a 10,000 fold dilution, and the variation of the amount of hemoglobin in the sample with lapse of time was observed. The results are shown in FIG. 2 of the accompanying drawings wherein the abscissa indicates the lapse of time (hour) and the ordinate indicates the concentration (%) of hemoglobin.

Figure 2:
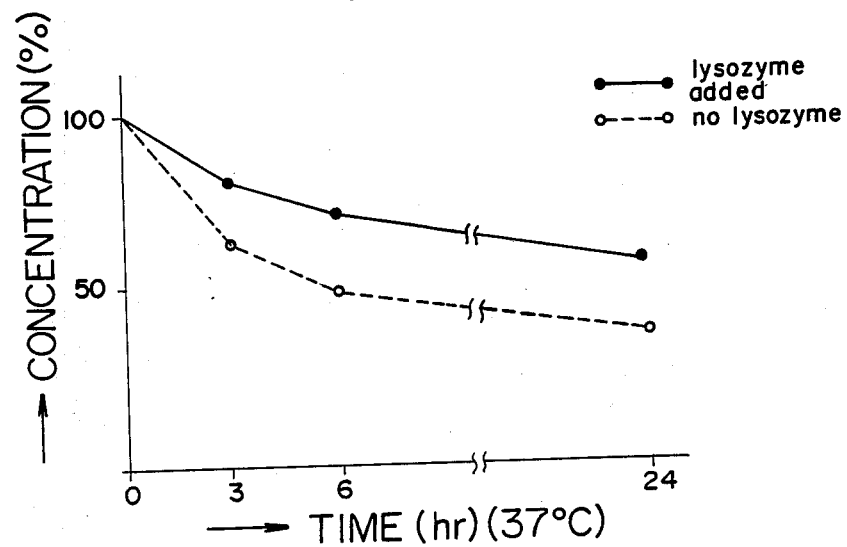

As is clear from FIG. 2 where the case using lysozyme is indicated by a solid line and the case not using lysozyme is indicated by a dotted line, the decomposition of hemoglobin is prevented by the action of lysozyme.

EXPERIMENT 3

Figure 3:
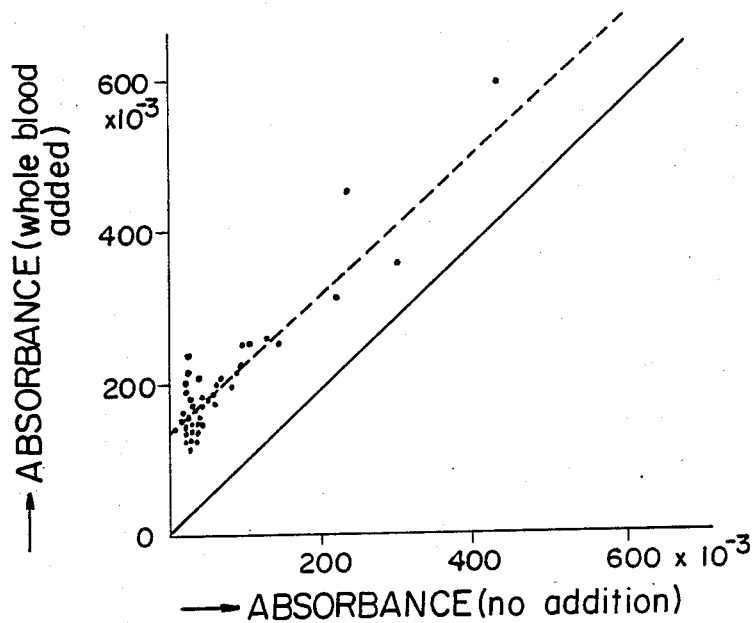

The absorbance attributable to transferrin in the concentrated aqueous feces (60 samples) was measured according to the ELISA method. A whole blood was added to each of the samples of faces to make a 30,000 fold dilution, and the absorbance was measured. The results are plotted in FIG. 3 of the accompanying drawings wherein the abscissa indicates the absorbance in the case with the whole blood and the ordinate indicates the absorbance in the case of no addition. Actually, there were some samples which originally contained some blood, but with addition of the whole blood thereto, the absorbance attributable to transferrin has increased in all those samples which exactly corresponded to the added whole blood.

Accordingly, it is understood that transferrin is measurable even in a small amount and advantageous for detection of occult blood in the feces.

EXPERIMENT 4

Figure 4:
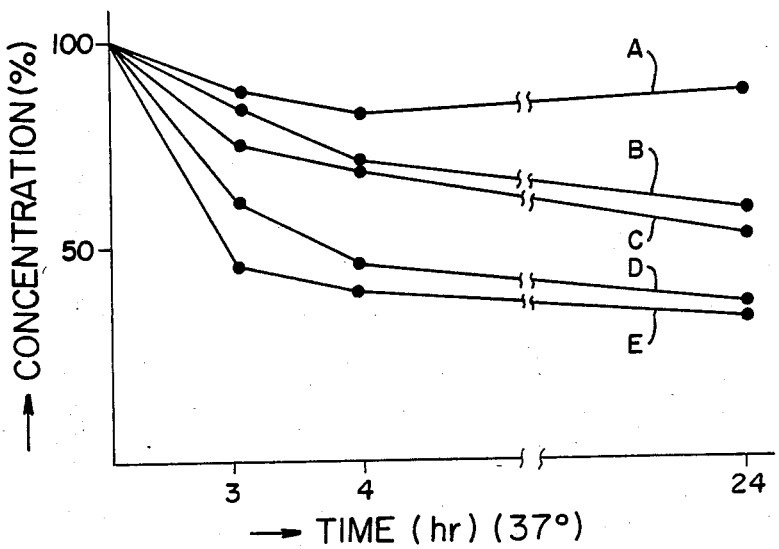

A whole blood was added to a 25 % aqueous fecal sample obtained by mixing the feces provided by 30 healthy persons to make a 10,000 fold dilution, and the variation of the amounts of various blood proteins in the sample with lapse of time was observed. The results are shown in FIG. 4 of the accompanying drawings wherein the abscissa indicates the lapse of time (hour) and the ordinate indicates the concentrations (%) of proteins. Curve A relates to transferrin; curve B relates to haptoglobin; curve C relates to albumin; curve D relates to hemoglobin; curve E relates to fibrinogen.

As is clear from FIG. 4, the proteins other than transferrin are decomposed with lapse of time by the action of intestinal bacteria, whereas transferrin is hardly decomposed and proven to be suitable for detection of occult blood.

Figure 5:
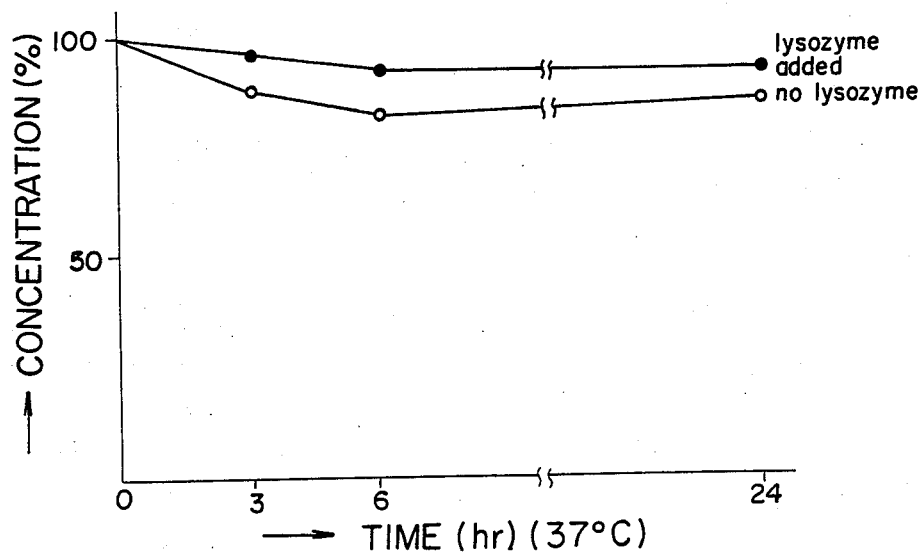

The decomposition status of transferrin was further observed with addition of lysozyme as the bacteriolytic enzyme, and the results are shown in FIG. 5 of the accompanying drawings wherein the abscissa indicates the lapse of time (hour) and the ordinate indicates the concentration (%) of transferrin. As is clear from FIG. 5 where the case using lysozyme is indicated by the line with filled in dots and the case not using lysozyme is indicated by line with open dots, the decomposition is more prevented with lysozyme.

EXPERIMENT 5

Figure 6:
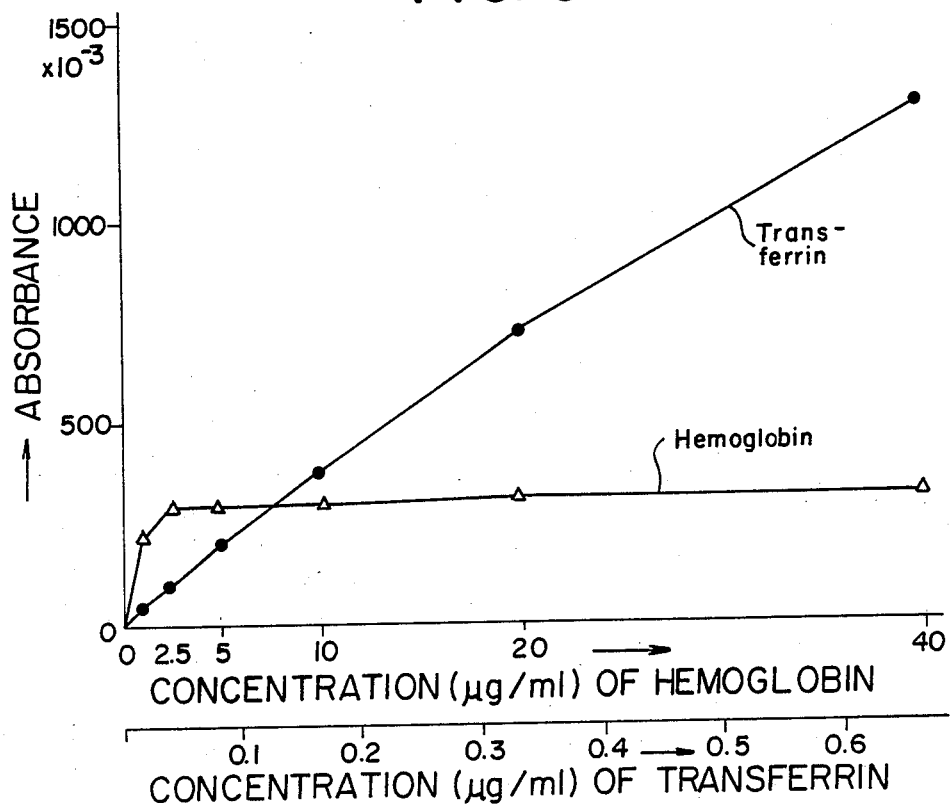

Samples of aqueous feces were mixed with whole blood in various concentrations, and the absorbance attributable to hemoglobin or transferrin was measured on each sample according to the ELISA method. The results are shown in FIG. 6 of the accompanying drawings wherein the abscissa indicates the concentration ($\mu$g/ml) of hemoglobin or transferrin and the ordinate indicates the absorbance. From this result, it is learned that hemoglobin is very sensitive up to the concentration of about 2.5 $\mu$g/ml, but then its absorbance is made constant at about 250 ($\times 10^{-3}$). On the other hand, transferrin shows a direct and proportional increase of absorbance with the increase of its concentration.

EXPERIMENT 6

Figure 7:
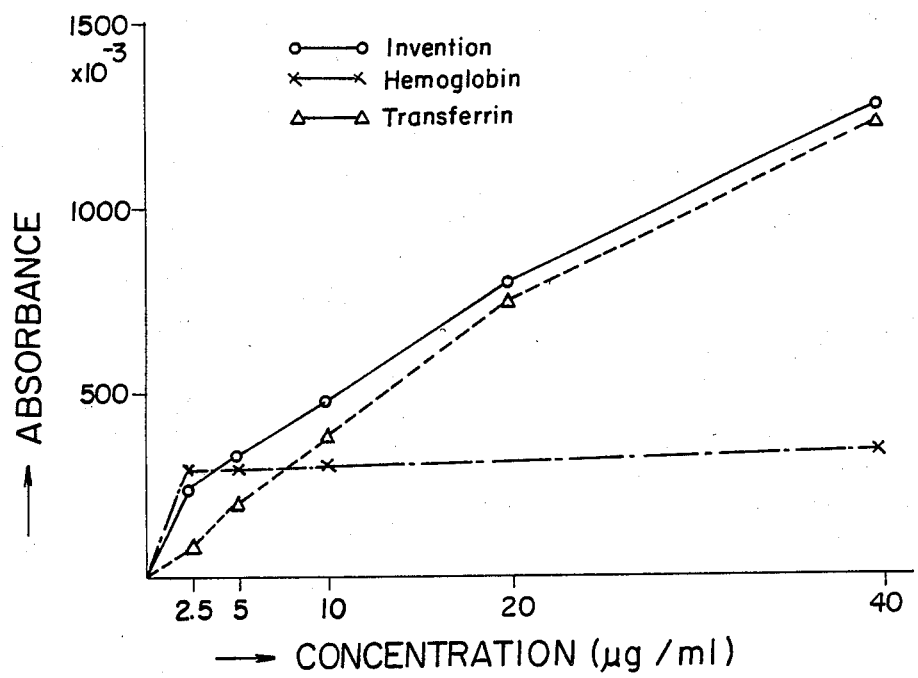

Using the same sample as prepared in Example 5, detection of hemoglobin and transferrin were respectively made. Further, the simultaneous detection of hemoglobin and transferrin according to the invention was similarly conducted. The results are shown in FIG. 7 of the accompanying drawings wherein the abscissa indicates the concentration ($\mu$g/ml) of hemoglobin and/or transferrin and the ordinate indicates the absorbance. It is thus clearly understood that over a wide range of concentration (i.e. from low to high concentrations) the occult blood in feces can be detected according to the invention method.

What is claimed is:

1. A method for detection of occult blood in a fecal sample comprising simultaneously reacting said fecal sample with antibodies to hemoglobin and antibodies to transferrin and determining the presence of immunologic reaction products of said hemoglobin and transferrin as an indication of the presence of occult blood.

2. The method according to claim 1, wherein the fecal sample is admixed with a glycosidase capable of lysing bacterial cell walls without decomposing hemoglobin prior to the determination of hemoglobin and transferrin.

3. The method according to claim 1, wherein the fecal sample is sampled by the use of a spoon or spatula coated with anti-human hemoglobin antibody and anti-human transferrin antibody.

4. The method according to claim 2, wherein the enzyme is lysozyme.

* * * * *